United States Patent
Zheng

(10) Patent No.: US 12,303,420 B2
(45) Date of Patent: May 20, 2025

(54) ADJUSTABLE SCOLIOSIS ORTHOSIS AND USE METHOD THEREOF

(71) Applicant: Yuxi Zheng, Beijing (CN)

(72) Inventor: Yuxi Zheng, Beijing (CN)

(*) Notice: Subject to any disclaimer, the term of this patent is extended or adjusted under 35 U.S.C. 154(b) by 71 days.

(21) Appl. No.: 18/138,543

(22) Filed: Apr. 24, 2023

(65) Prior Publication Data

US 2023/0404787 A1    Dec. 21, 2023

Related U.S. Application Data

(63) Continuation of application No. PCT/CN2022/103043, filed on Jun. 30, 2022.

(30) Foreign Application Priority Data

Jun. 15, 2022   (CN) .......................... 202210680464.6

(51) Int. Cl.
*A61F 5/02* (2006.01)

(52) U.S. Cl.
CPC .................................. *A61F 5/024* (2013.01)

(58) Field of Classification Search
CPC .............. A61F 5/02–03; A61F 5/04–34; A61F 13/04–048; A61B 17/12; A61B 17/132–1355
See application file for complete search history.

(56) References Cited

U.S. PATENT DOCUMENTS

| | | | | |
|---|---|---|---|---|
| 41,749 A * | 3/1864 | Andrews | ................... | A61F 5/34 128/118.1 |
| 347,171 A * | 8/1886 | Giralt | ........................ | A61F 5/32 128/105.1 |
| 551,237 A * | 12/1895 | Stewart | ..................... | A61F 5/24 128/100.1 |
| 1,676,657 A * | 7/1928 | Luzzi | ........................ | A61F 5/24 128/100.1 |
| 2,512,081 A * | 6/1950 | Young | ...................... | A61F 13/04 425/2 |
| 3,332,415 A * | 7/1967 | Ericson | ............... | A61F 5/05816 128/DIG. 20 |
| 6,629,942 B1 | 10/2003 | Tubbs | | |
| 2006/0000478 A1* | 1/2006 | Taylor | ..................... | A61F 5/026 128/869 |

(Continued)

FOREIGN PATENT DOCUMENTS

| CN | 201361161 Y | 12/2009 |
|---|---|---|
| CN | 102026594 A | 4/2011 |

(Continued)

*Primary Examiner* — Michelle J Lee
(74) *Attorney, Agent, or Firm* — SZDC Law PC

(57) ABSTRACT

An adjustable scoliosis orthosis includes: an orthosis body sleeved on the outside of a user's torso in a ring shape, with its inner wall fitted to the user's torso, and provided with an opening for the torso to enter and exit, wherein a through mounting hole is provided at a designated position on the orthosis body; a connecting structure for connecting both sides of the opening of the orthosis body; and an adjustment device arranged at the mounting hole and comprising an airbag structure. The airbag structure is at least partially arranged inside the orthosis body and is fitted to the user's torso to exert a pressing force that is positively correlated with the internal gas pressure of the airbag structure.

12 Claims, 13 Drawing Sheets

(56) References Cited

U.S. PATENT DOCUMENTS

2009/0287128 A1    11/2009  Ingimundarson
2014/0135672 A1 *  5/2014   Joseph .................... A61F 5/028
                                                          602/19

FOREIGN PATENT DOCUMENTS

| CN | 111588528 A |   | 8/2020  |          |           |
|----|-------------|---|---------|----------|-----------|
| CN | 211433544 U |   | 9/2020  |          |           |
| CN | 112168448 A |   | 1/2021  |          |           |
| CN | 215131037 U |   | 12/2021 |          |           |
| GB | 2360944 A   | * | 10/2001 | ............. | A61F 5/024 |

\* cited by examiner

_US 12,303,420 B2_

1

ADJUSTABLE SCOLIOSIS ORTHOSIS AND USE METHOD THEREOF

This application is the Continuation Application of PCT/CN2022/103043, filed on Jun. 30, 2022, which claims priority to Chinese Patent Application No. 202210680464.6, filed on Jun. 15, 2022, which is incorporated by reference for all purposes as if fully set forth herein.

TECHNICAL FIELD

The present invention relates to the technical field of orthopedic devices, in particular to an adjustable scoliosis orthosis and use method thereof.

BACKGROUND

Studying at desks and using electronic products for a long time are common for teenagers. If teenagers develop some bad sitting habits, in the long run, it will lead to scoliosis in the spine of teenagers, which will seriously affect their health. Therefore, once scoliosis occurs, it is necessary to correct it in time.

The current scoliosis correction method is generally to use orthosis for physical correction. The orthosis is formed by 3D printing and then worn on the user's torso to exert a certain pressure to specific parts of the torso to achieve the correction effect. Each orthosis must be customized according to the patient's scoliosis conditions and can only be kept in a fixed shape after being made. However, the user's spine will be gradually corrected with elapse of the wearing time and the force exerted by the orthosis that can only maintain a fixed shape will become weaker and weaker, resulting in the gradual deterioration of the correction effect. Since the orthosis itself does not have adjustment function, it is necessary to customize a new orthosis, which will impose a great economic burden on the user.

SUMMARY

The present invention provides an adjustable scoliosis orthosis to effectively solve the problems discussed above. The invention also provides a method for using the adjustable scoliosis orthosis.

To this end, the present invention provides an adjustable scoliosis orthosis, comprising:
  an orthosis body sleeved on the outside of a user's torso in a ring shape, with its inner wall fitted to the user's torso, and provided with an opening for the torso to enter and exit, wherein a through mounting hole is provided at a designated position on the orthosis body;
  a connecting structure for connecting both sides of the opening of the orthosis body; and
  an adjustment device arranged at the mounting hole and comprising an airbag structure, wherein the airbag structure is at least partially arranged inside the orthosis body and is fitted to the user's torso to exert a pressing force that is positively correlated with the internal gas pressure of the airbag structure.

Further, the connecting structure comprises two external structures and an adjustment structure arranged on both sides of the opening of the orthosis body.
  wherein the adjustment structure is connected to the external structure to adjust the size of the opening of the orthosis body indirectly through the external structure.

Further, the external structure is a velcro.

2

The adjustment structure comprises two flexible structures, a tightening belt and a winding wheel, wherein the two flexible structures are respectively connected to the two external structures through corresponding velcro and provided with perforations thereon, wherein the tightening belt is arranged to run through the perforations to realize distance adjustment of the two flexible structures during tension adjustment, wherein an end of the tightening belt is wound and fixed by the winding wheel, and wherein the winding wheel is fixedly connected to the orthosis body to adjust the tension of the tightening belt by adjusting the winding length of the tightening belt.

Further, the internal gas pressure of the airbag structure is adjusted by changing the internal space.

Further, the internal gas pressure of the airbag structure is adjusted by changing the internal gas volume.

Further, the airbag structure is an annular airbag, and the adjustment device further comprises a connecting seat, a pressing rod and a fixing structure, wherein the connecting seat is fixedly connected to the orthosis body, wherein the pressing rod extends through the connecting seat, with one end of the pressing rod extending into the interior of the orthosis body, which end is provided with a press disc, wherein the annular airbag is sleeved on the pressing rod and is located between the press disc and the connecting seat, with only part of the end face of the annular airbag being fitted with the press disc, and wherein the fixing structure is arranged to fix the relative position of the pressing rod and the connecting seat.

Further, a countersunk structure is arranged in the middle of the annular airbag, into which the press disc fully extends.

Further, the outermost diameter of the annular airbag is larger than the diameter of the mounting hole.

Further, the outermost diameter of the annular airbag is designated as A, and the diameter of the press disc is designated B, then A>B>A/2.

Further, the press disc is provided with a flexible structure on the surface facing the orthosis body.

Further, a threaded section is provided on the side of the pressing rod and a threaded hole is provided in the center of the connecting seat, the threaded section screwed into the threaded hole to form the fixing structure.

Further, the orthosis further comprises a limit block, and an end of the pressing rod that is distal from the press disc extends out of the threaded hole, to which end the limit block is fixedly connected.

Further, the connecting seat is provided with a through hole, wherein the side wall of the through hole is provided with a snap slot, wherein a plurality of snap rings are provided on the side of the pressing rod, one of the plurality of snap rings snapped with the slot to form the fixing structure.

Further, the orthosis body is provided with a plurality of hollow holes.

Further, the airbag structure comprises an inflation end for gas volume adjustment by supplying gas in and out of the interior of the airbag.

The present invention also provides a method for using an adjustable scoliosis orthosis, which is applicable to the above described adjustable scoliosis orthosis, comprising the following steps:
  causing a user to put on an orthosis body without mounting holes, marking the position of the mounting holes according to correction needs of the user's torso, and then removing the orthosis body to machine the mounting holes; and fixing an adjustment device at the position where the mounting holes are provided.

With the technical solutions of the present invention, the following technical effects can be achieved.

1. With the adjustable scoliosis orthosis of the present invention, it is more flexible and convenient to apply force to the local parts of the human body through the provision of the airbag structure, so that the torso naturally produces a tendency to change towards the correct posture after feeling the pressing force, realizing the correction function, and the pressing force of the airbag structure can be adjusted in various ways.

2. The provided fabric structure makes the appearance more beautiful and can achieve a better positioning effect by the local covering of the body and/or the covering of the orthosis body, and improve the comfort of use.

3. The orthosis is provided with a specific form of adjustment device on the orthosis body. The annular airbag is pressed by the press disc of the pressing rod in the adjustment device, so that the gas in the annular airbag is pressed to the internal part of the annular airbag against the outside and deforms and bulges the annular airbag. By adjusting the degree of pressing of the press disc on the annular airbag and then adjusting the degree of bulging of the annular airbag, the adjustment function is realized, making the orthosis adaptable to the orthotic needs of the user in different periods, and reducing the financial burden on the user. At the same time, such adjustment using the press disc can avoid the installation of additional devices to inflate and deflate the annular airbag, simplifying the structure of the adjustment device and improving the comfort of the user when wearing it.

4. When the gas volume inside the airbag structure can be adjusted, the pressure can be increased quickly through the external gas source, and reduced conveniently through deflation, so that the effect on different human bodies is more targeted.

5. In use, the orthosis body and mounting holes of the orthotic are not formed at the same time. Instead, the orthotic body is made by 3D printing first, and then provided with the mounting holes to prevent the deviation of the mounting hole position caused by the deviation between the actual printed product and the designed product when 3D printing the orthosis body, thus ensuring that the position of the mounting hole is more in line with the actual orthotic needs. A wide range of materials can be selected for the orthosis body to achieve better comfort.

DESCRIPTION OF THE DRAWINGS

In order to more clearly illustrate the embodiments of the present invention or the technical solutions in the prior art, the accompanying drawings to be used in the description of the embodiments or prior art will be briefly described below. It is obvious that the accompanying drawings in the following description are only some of the embodiments recorded in the present invention, and other accompanying drawings can be obtained according to these accompanying drawings without creative work for those of ordinary skill in the art.

DESCRIPTION OF THE EMBODIMENTS

The technical solutions in the embodiments of the present invention will be described clearly and completely in conjunction with the accompanying drawings in the embodiments of the present invention. Obviously, the described embodiments are only a part of the embodiments of the present invention, rather than all the embodiments.

In the description of the present invention, it should be noted that the orientation or positional relationships indicated as "center", "top", "bottom", "left", "right", "vertical", "horizontal", "inside", "outside", etc., are based on the orientation or positional relationships shown in the attached drawings and are intended only to facilitate and simplify the description of the invention, not to indicate or imply that the device or element referred to must have a particular orientation, be constructed and operated in a particular orientation, and therefore cannot be construed as a limitation of the present invention.

Embodiment 1

Figure 1:
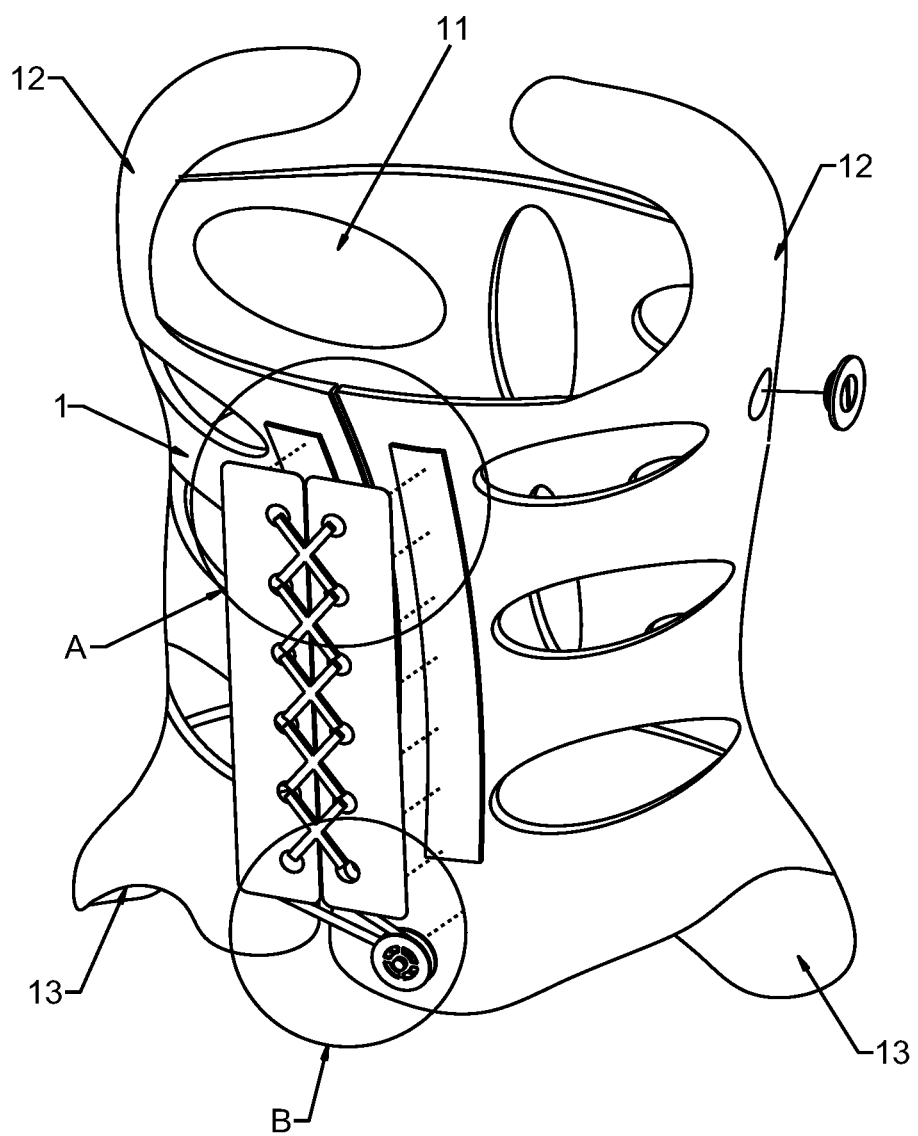
FIG. 1 is an exploded schematic diagram of the orthosis body, adjustment structure and connecting structure of the adjustable scoliosis orthosis according to the present invention.
Figure 2:
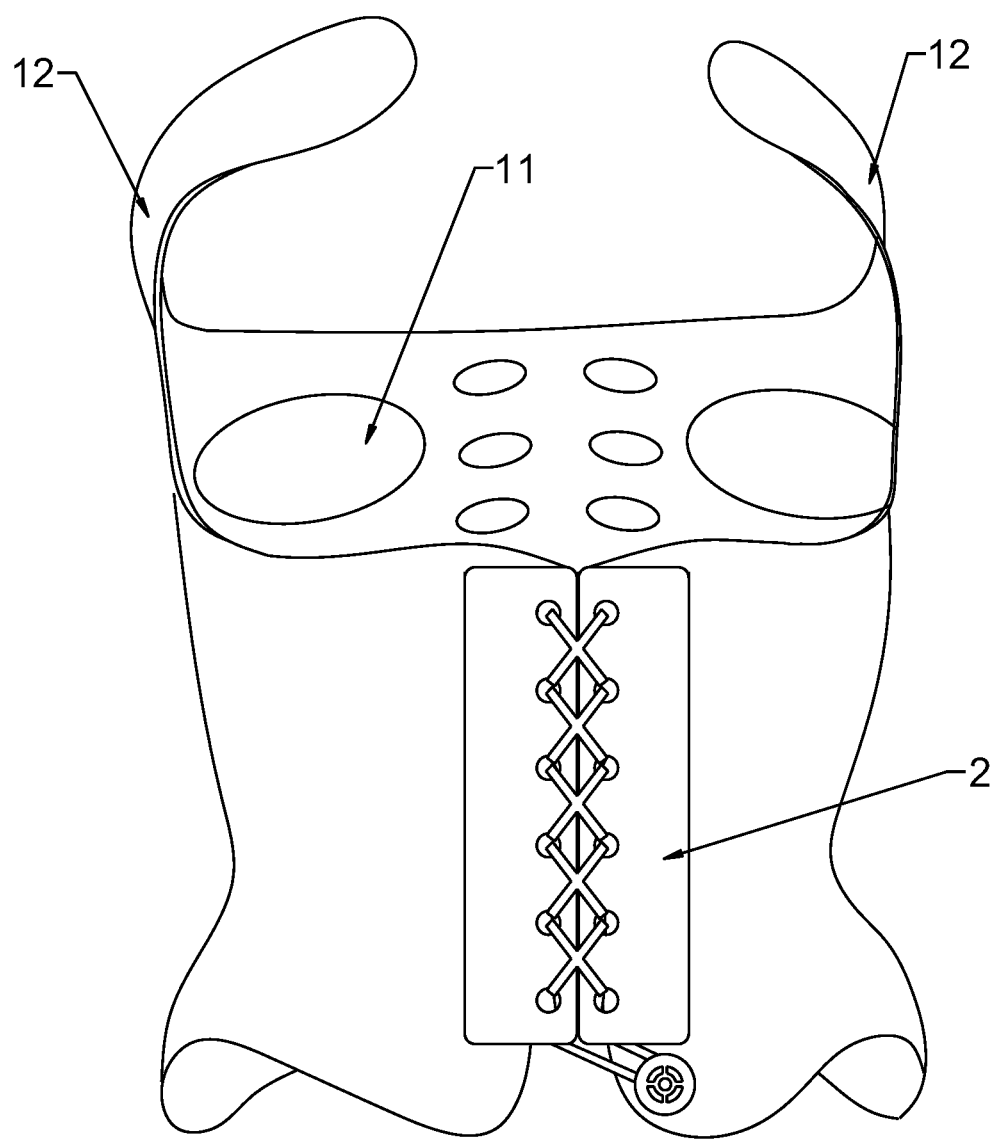
FIG. 2 is a schematic diagram of the connection of the orthosis body and the connecting structure of the adjustable scoliosis orthosis according to the present invention.
Figure 3:
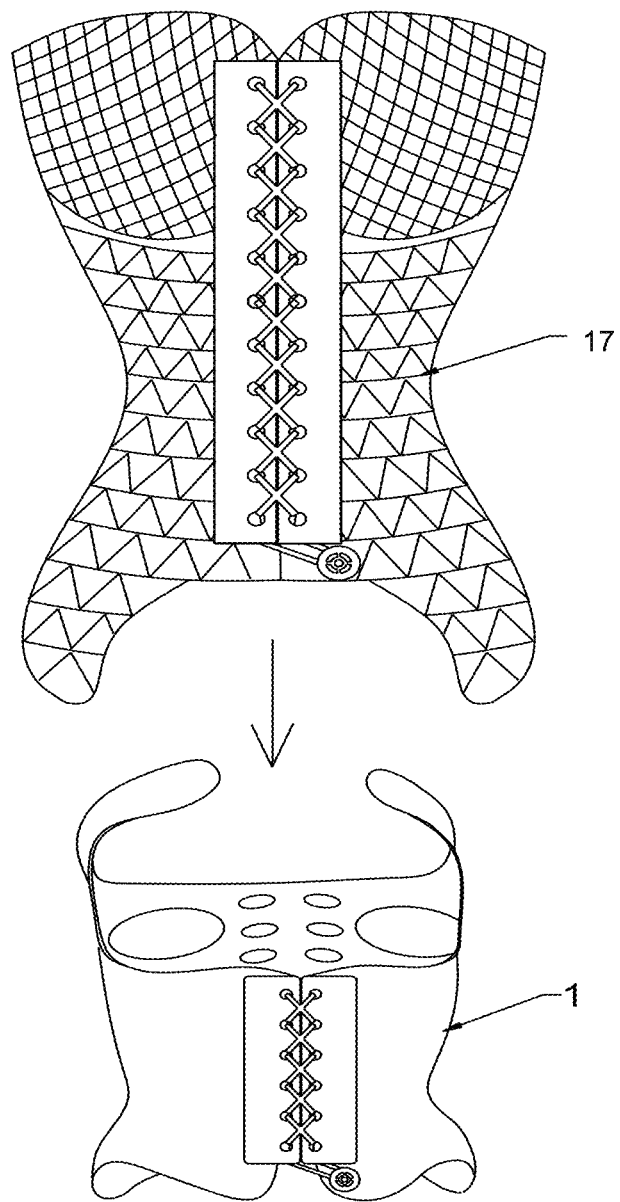
FIG. 3 is an exploded schematic diagram of the fabric structure and the orthosis body.
Figure 6:
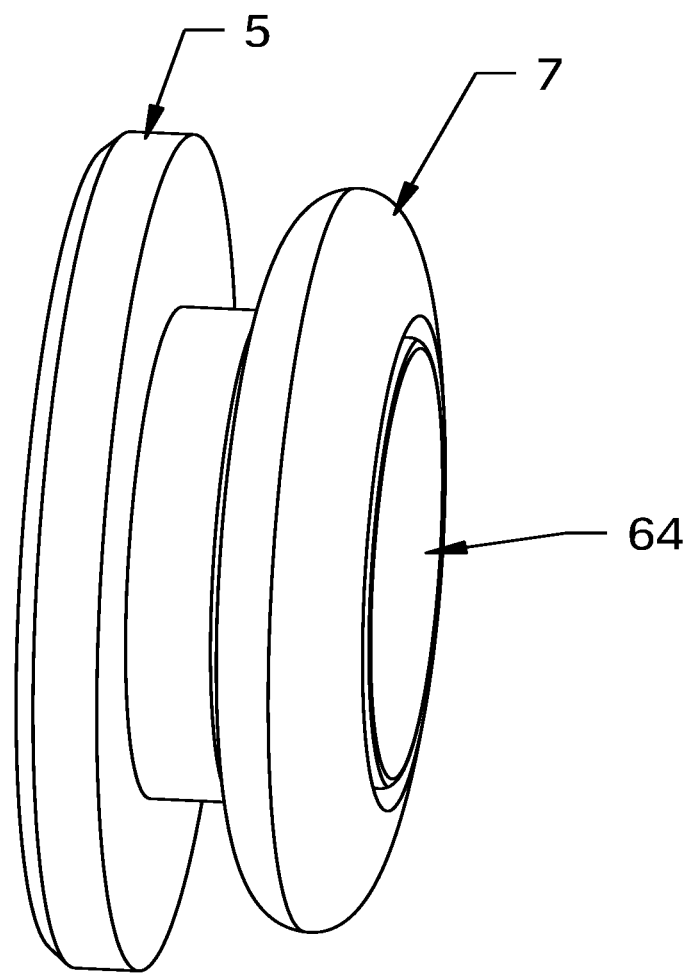
FIG. 6 is a schematic diagram of the structure of the adjustment device in Embodiment 2.
Figure 7:
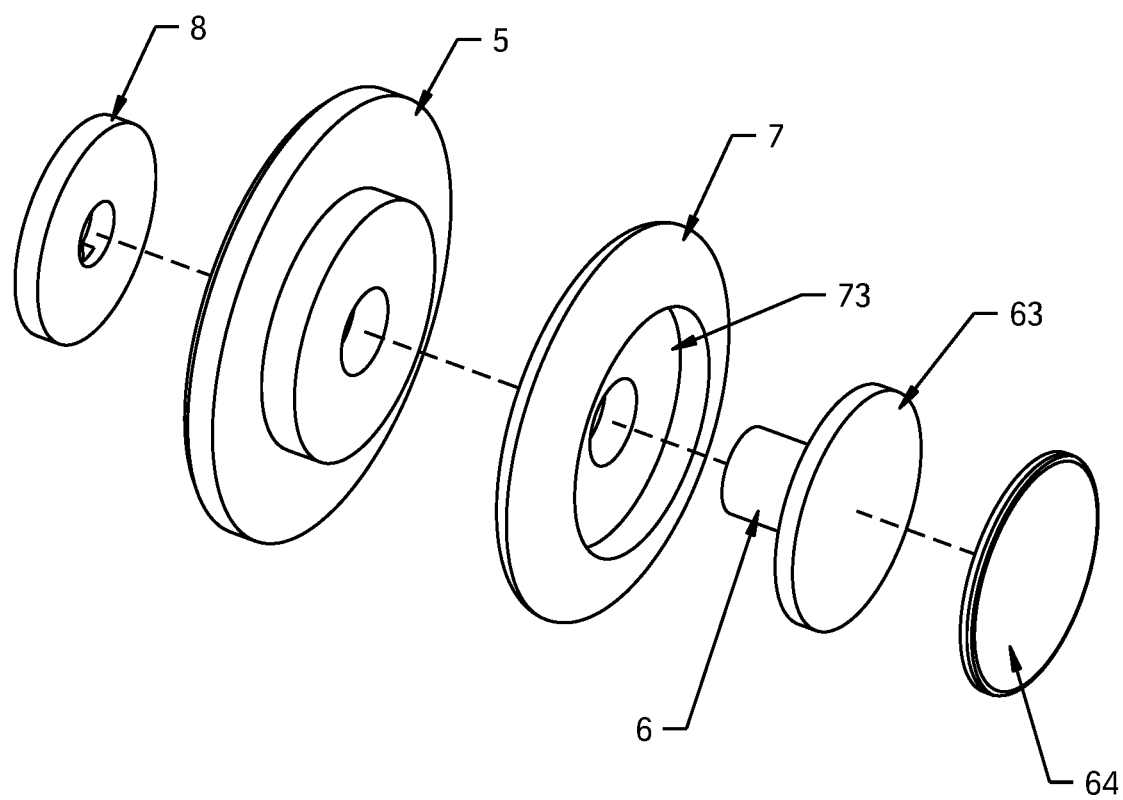
FIG. 7 is an exploded view of the components of the adjustment device in Embodiment 2.

The present invention relates to an adjustable scoliosis orthosis, as shown in FIGS. 1-3, comprising:
an orthosis body 1 sleeved on the outside of a user's torso in a ring shape, with its inner wall fitted to the user's torso, and provided with an opening for the torso to enter and exit, wherein a through mounting hole is provided at a designated position on the orthosis body 1; a connecting structure 2 for connecting both sides of the opening of the orthosis body 1; and an adjustment device arranged at the mounting hole and comprising an airbag structure 7 (see FIGS. 6 and 7), wherein the airbag structure 7 is at least partially arranged inside the orthosis body 1 and is fitted to the user's torso to exert a pressing force that is positively correlated with the internal gas pressure of the airbag structure 7.

In order to achieve better correction effects, the orthosis body 1 in the present invention may be provided with an armpit support part 12 and a pelvic support part 13. During use, these two parts need to adapt to different users' postures, so as to achieve a good fit with the armpit and pelvis of the user and ensure leveling of the pelvis and armpit, which is crucial for the correction of the spine.

To increase the aesthetics of the product, as shown in FIG. 3, a fabric structure 17 is provided to completely wrap around the exterior of the orthosis body 1, so that the orthosis body 1 can be used as a frame for installation of the adjustment device to achieve the correction purpose, as well as so that the fabric structure 17 can be used as an external decorative material to achieve aesthetic effects. At the same time, the tightening of the fabric structure 17 can make the orthosis body 1 keep a better fit with the user's torso. Preferably, an opening is also provided on the fabric structure 17 and a connecting structure 2 is also used to realize the connection of both sides of the opening, facilitating wearing and use.

In the present invention, the connecting structure 2 may be implemented in form of a threadlike structure. Perforations are formed on both sides of the opening of the orthosis body 1 and the connecting structure 2 runs through the perforations. By means of knotting the ends of the connecting structure, or by means of an additional fixing piece or by means of a winding structure, the connecting structure is fixed to avoid the occurrence of loosening. Alternatively, a plurality of connecting structures 2 may be used, each responsible for a certain distance in the height direction of the human body. As compared with the single connecting structure 2, the plurality of connecting structures 2 makes it easier to control the fitting degree of the orthosis body 1 relative to the user's torso. In this case, since the travel of the connecting structure 2 is relatively long, it is preferably not elastic and the degree of fixation of the orthosis is adjusted through the degree of tensioning of the connecting structure 2.

In the above implementation, the way in which the threadlike structure is fixed as described above is only a less expensive way of implementation. As far as the present invention is concerned, other ways are also within the protection scope of the present invention, such as velcro, zipper and hook and loop that can be directly connected to the orthosis body 1 to achieve the predetermined connection function.

Figure 4:
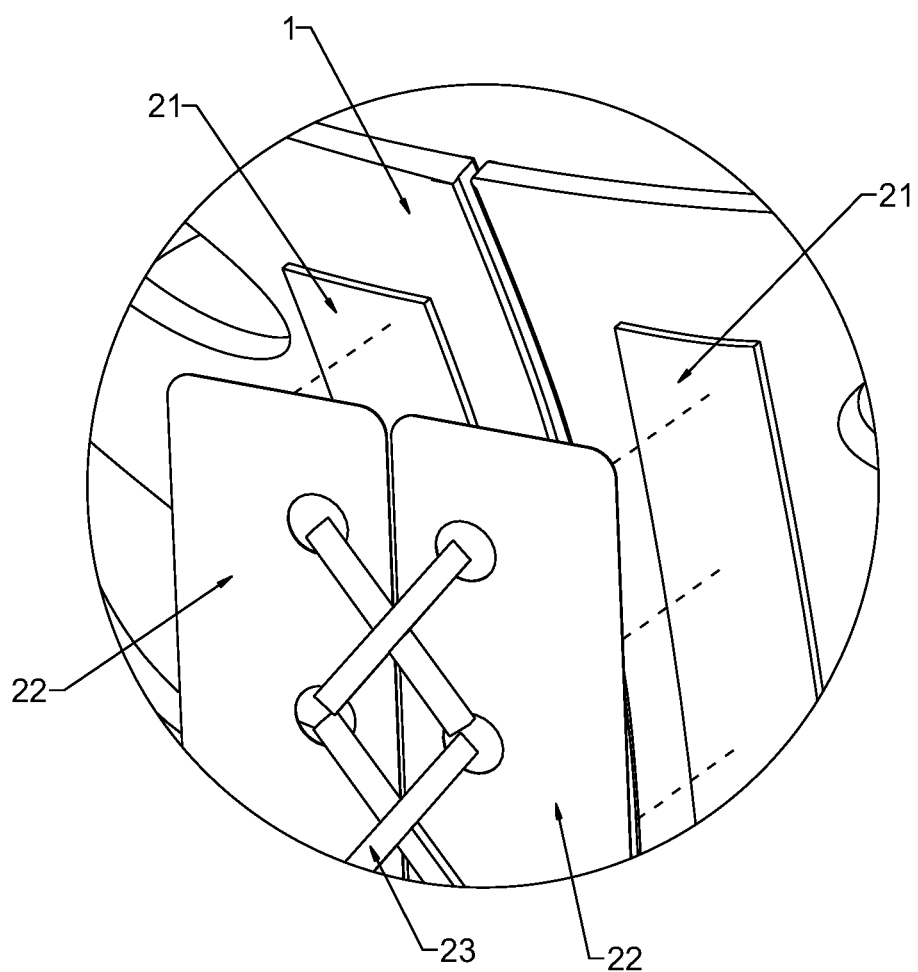
FIG. 4 is a partially enlarged view at A in FIG. 1.
Figure 5:
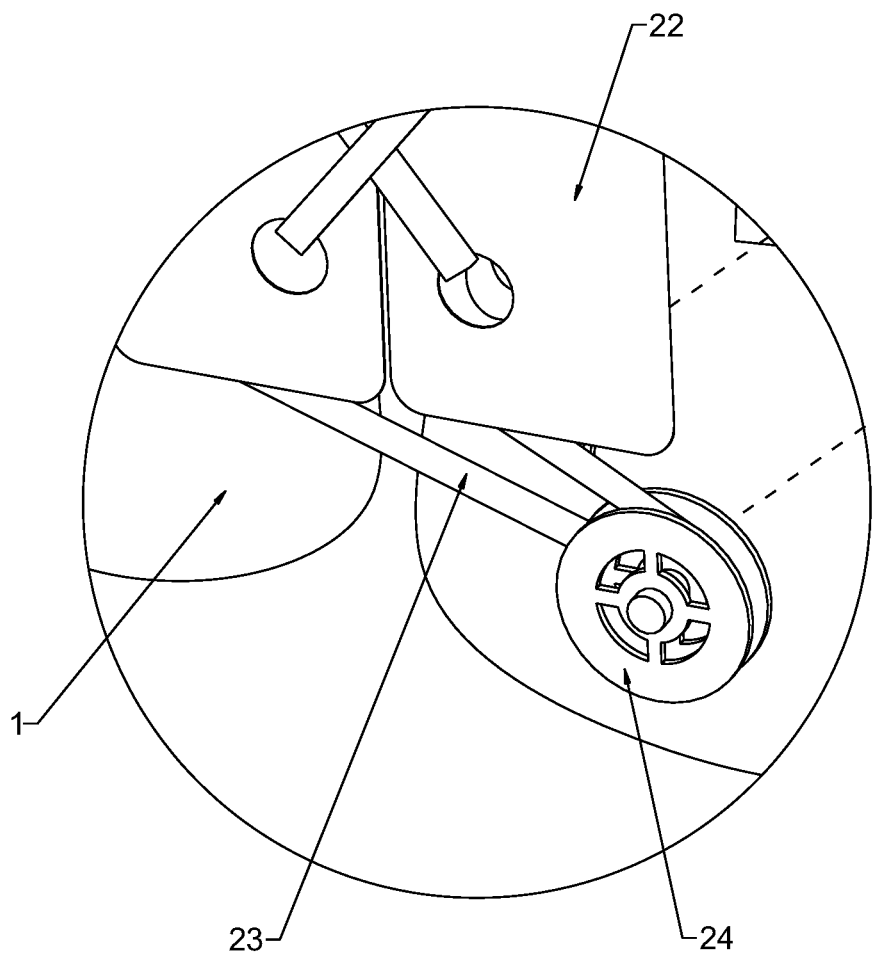
FIG. 5 is a partially enlarged view of FIG. 1 at B.

As shown in FIGS. 4 and 5, as another way to avoid perforating and make adjustment easier, the connecting structure 2 comprises two external structures 21 provided on both sides of the opening of the orthosis body 1. The external structures 21 and the orthosis body 1 may be fixed by any means such as pasting, hot pressing or sewing, depending on the characteristics of materials used. The connecting structure 2 further comprises an adjustment structure connected to the external structures 21 to indirectly adjust the size of the opening of the orthosis body 1 through the external structures 21. When it is necessary to remove the orthosis body 1, disconnect the adjustment structure and the external structures 21, so that the open ends of the orthosis body 1 can be opened freely.

In the case where the external structures 21 adopt velcro, the adjustment structure comprises two flexible structures 22, a tightening belt 23 and a winding wheel 24, wherein the two flexible structures 22 are respectively connected to the two external structures 21 through corresponding velcro and provided with perforations thereon, wherein the tightening belt 23 is arranged to run through the perforations to realize distance adjustment of the two flexible structures 22 during tension adjustment, wherein an end of the tightening belt 23 is wound and fixed by the winding wheel 24, and wherein the winding wheel 24 is fixedly connected to the orthosis body 1 to adjust the tension of the tightening belt 23 by adjusting the winding length of the tightening belt 23.

As shown in FIGS. 4 and 5, in the above preferred implementation, the external structures 21 and the winding wheel body 24 can always maintain a fixed connection with the orthosis body 1, while the connection of the flexible structures 22 and the external structures 21 and the connection of the end of the tightening belt 23 and the winding wheel 24 can be realized after binding of the flexible structures 22 and the tightening belt 23. After the above steps are completed, the tightening belt 23 obtains the initial tension. As a finer adjustment process, the degree of fixation of the orthosis body 1 relative to the human body can be finely adjusted by performing the winding or unwinding action on the winding wheel 24.

Embodiment 2

As a preferred implementation of the Embodiment 1, the internal gas pressure of the airbag structure 7 is adjusted by changing the internal space.

In this case, as a specific implementation, the airbag structure 7 is an annular airbag and, as shown in FIGS. 6-9, the adjustment device further comprises a connecting seat 3, a pressing rod 6 and a fixing structure, wherein the connecting seat 3 is provided with a flange structure that can be fixed to the outer wall of the orthosis body 1 by riveting or gluing, wherein the pressing rod 6 extends through the connecting seat 3, with one end of the pressing rod 6 extending into the interior of the orthosis body 1, which end is provided with a press disc 63, wherein the annular airbag 7 is sleeved on the pressing rod 6 and is located between the press disc 63 and the connecting seat 3, and only part of the end face of the annular airbag is fitted with the press disc, and wherein the fixing structure is arranged to fix the position of the pressing rod 6 relative to the connecting seat 3, so that the press disc 63 can maintain the pressing on the annular airbag 7. The orthosis may be provided with a plurality of adjustment devices, and a plurality of mounting holes corresponding to the number of adjustment devices. The specific number and position of the adjustment devices and mounting holes can be determined according to the user's needs.

Figure 8:
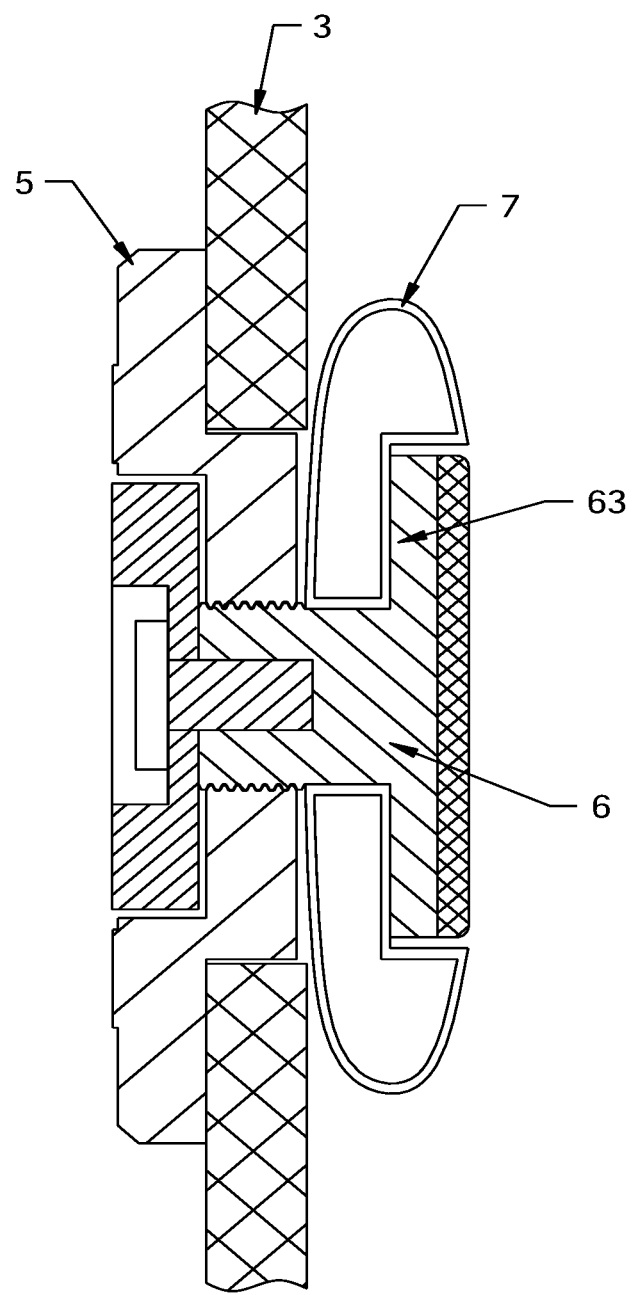
FIG. 8 is a cross-sectional view of the adjustment device in Embodiment 2 (state before pressing of the press disc)
Figure 9:
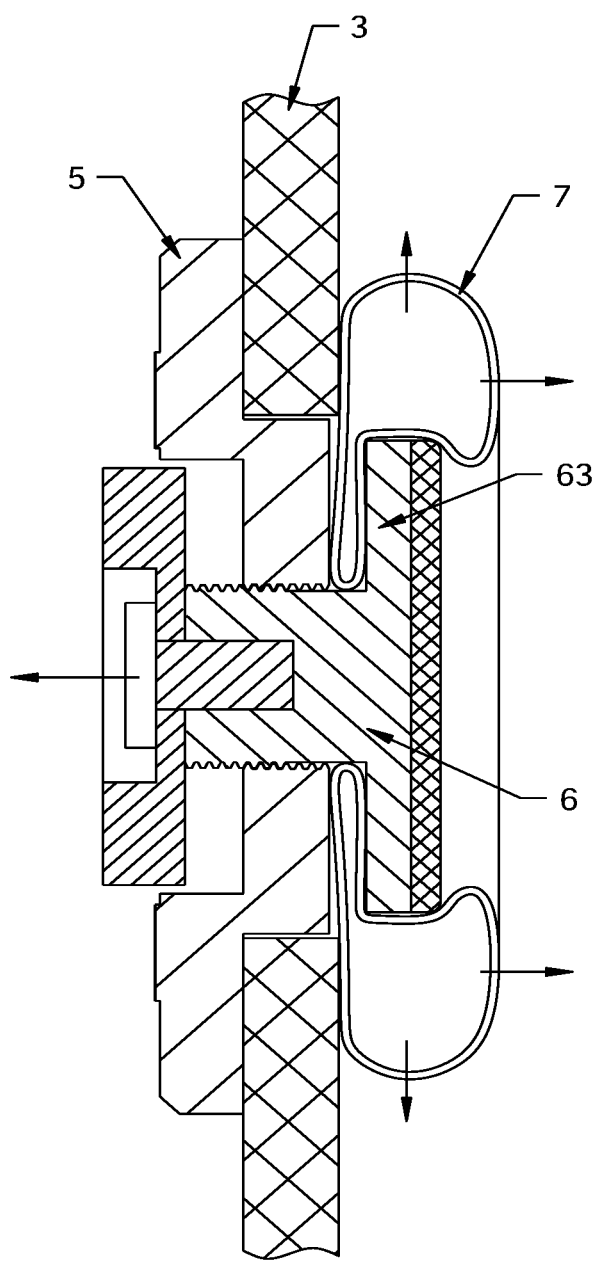
FIG. 9 is a cross-sectional view of the adjustment device in Embodiment 2 (state after pressing of the press disc)

The specific adjustment process of the orthosis of the above embodiment will be described below. After the user wears the orthosis body 1, as shown in FIGS. 8 and 9, the pressing rod 6 drives the press disc 63 to press the annular airbag 7 along the direction extending through the connecting seat 3 relative to the user's torso, in order to press the gas in the annular airbag 7 between the pressing rod 6 and the connecting seat 3 towards the edge of the annular airbag 7, so that the air pressure at the edge increases and causes the edge of the annular airbag 7 to deform and bulge, thus the end face of the edge of the annular airbag 7 facing the user moves towards the user, realizing the function of applying a force to the user's body. The greater the distance that the pressing rod 6 moves outwards, the greater the pressing of the press disc 63 on the annular airbag 7 is, and the greater the moving distance of the end face of the annular airbag 7 is. In this way, the orthosis can realize the adjustment function by adjusting the position of the pressing rod 6, so that the orthosis can adapt to the correction needs of users in different periods.

Figure 12:
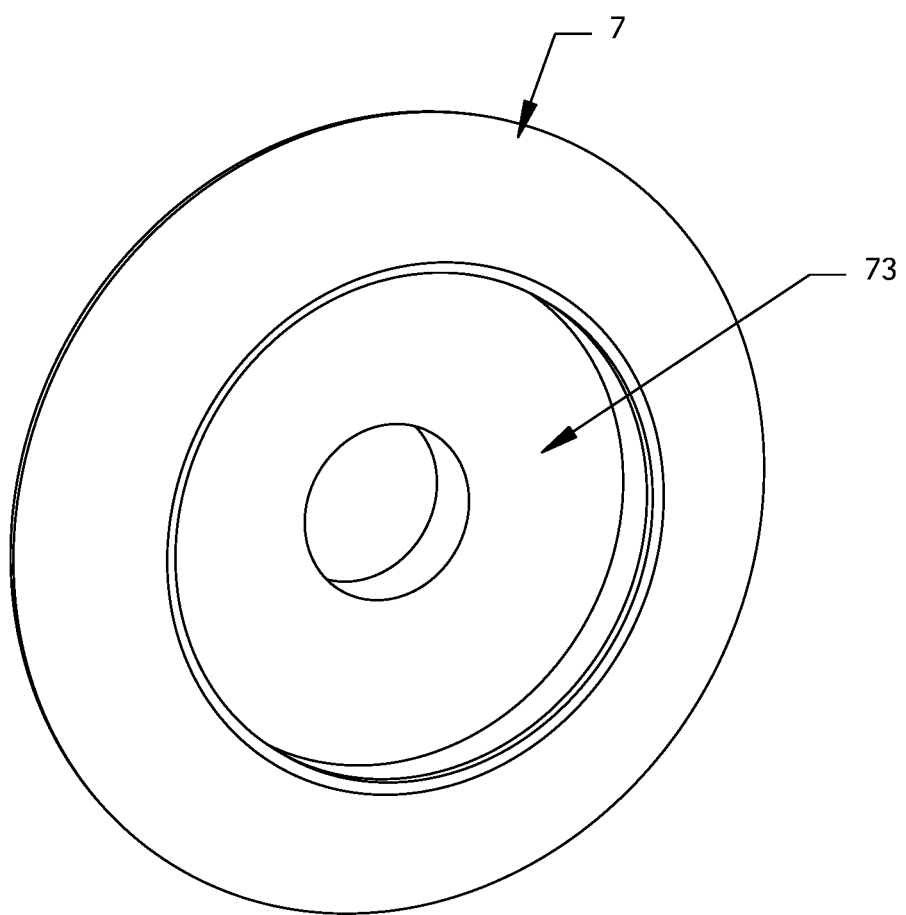
FIG. 12 is a structural representation of the annular airbag in Embodiment 2 and 3.

In order to maintain pressing on the annular airbag 7, the press disc 63 is generally configured as a relatively hard structure, which may affect the wearing comfort of the user. Therefore, as shown in FIG. 12, a countersunk structure 73 is preferably provided in the middle of the annular airbag 7. The depth of the countersunk structure 73 is greater than the thickness of the press disc 63, so that the press disc 63 can fully extend into the countersunk structure 73, avoiding direct contact with the user's torso. And, in the process of pressing the annular airbag 7 by the press disc 6, the outer side of the annular airbag 7 will easily fall into the countersunk structure 73 when it bulges, thus wrapping the end face of the press disc 63 and further preventing the press disc 63 from contacting the user, thereby enhancing the wearing comfort of the user.

The size of the press disc 63 directly determines the amount of gas pressed in the annular airbag 7, which in turn determines the degree of bulging of the annular airbag 7. The outermost diameter of the annular airbag 7 is designated as A, and the diameter of the press disc 63 is designated as B, then the size of the press disc 63 is preferably set to A>B>A/2, so that the volume of gas that the press disc 63 can press is sufficient to ensure deformation and bulging of the outer side of the annular airbag 7 and to ensure that the deformation area of the outer side of the annular airbag 7 is large enough to provide a better fit to the user's torso.

Figure 10:
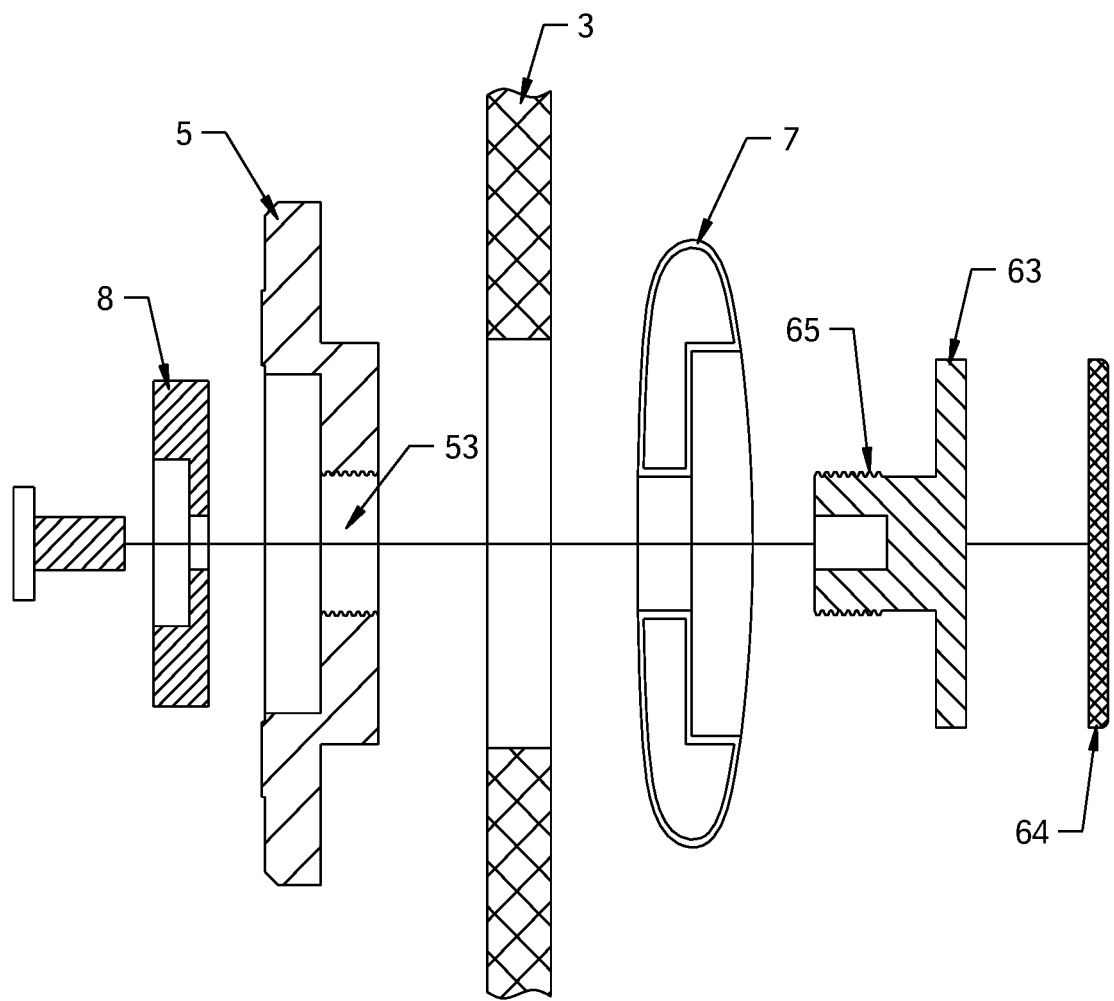
FIG. 10 is an exploded cross-sectional view of the components of the adjustment device in Embodiment 2.

The size of the press disc 63 in this structure is relatively large. Depending on the position and quantity of the adjustment devices installed for different users, as well as the physical conditions of different users, it may happen that the press disc touches the user. In order to avoid this situation, the thickness of the press disc 63 can be reduced as much as possible, and/or the depth of the countersunk structure 73 can be increased. However, in the practical application, in order to ensure the aesthetic appearance of the entire orthosis, the thickness of the entire adjustment device is often limited within a certain range. Therefore, as another means to avoid the discomfort caused by the press disc 63 contacting the user in a very small chance, in the present invention it is preferable to provide a flexible structure 64 on the surface of the press disc 63 facing the orthosis body 1, as shown in FIG. 10. The flexible structure 64 is usually a soft patch such as rubber or sponge, which is pasted on the surface of the press disc 63 facing the orthosis body 1 to separate the hard press disc 63 from the user, thereby improving the user's comfort. More preferably, 3A/4>B>A/2, which results in a better area or range of fit of the entire annular airbag 7 to the human body. Another advantage of the present invention is that the contact with the human body through the annular flexible area in the present invention is more comfortable than the prior art in which the pressing force is applied to a centralized position. At the same time, it is important to emphasize that the annular force application position formed in the present invention itself has an adaptive deformation capability, which can be achieved by redistribution of the gas in the annular airbag 7. In view of the homogeneity of the air pressure within the airbag, the forces applied to various parts of the human body by the annular airbag 7 after the adaptive deformation are equal. Through the above-mentioned optimization and improvements, the corrective force felt by the human body is more in line with its own body posture while achieving the required force level.

In the actual application of the orthosis, when the orthosis body 1 ensures sufficient fitting force with respect to the human body, the degree of deformation of the annular airbag 7 generated by the entire adjustment device during the adjustment process is limited, and the acceptance of the above deformation by the torso is to be achieved gradually in the process of long-term correction. In the present invention, the degree of deformation of the annular airbag 7 is sufficient to meet the above adjustment range. Of course, in order to increase the effectiveness of the use of the orthosis, a variety of models of adjustment devices can be provided, or a variety of models of annular airbags 7 and/or pressing rods 6 can be provided for the same type of adjustment device in order to meet various needs through targeted selection.

The outermost diameter of the annular airbag 7 is preferably larger than the diameter of the mounting hole. Thus, it is the inner wall of the orthosis body 1 that is pressed by the outer side of the annular airbag 7 when it is deformed, and the pressing on the connecting seat 3 is reduced. The outer side of the annular airbag 7 and the flange structure of the connecting seat 3 can cooperate with each other to form together a structure that can clamp the orthosis body 1, thus effectively preventing the connection seat 3 from falling off from the orthosis body 1.

In order to increase the breathability of the orthosis body 1 when worn, a plurality of hollow holes 11 (see FIGS. 1 and 2) are preferably provided on the orthosis body 1, and the hollow holes 11 are preferably formed after the formation of the mounting holes. The position and shape of the hollow holes 11 should be arranged so that the hollow holes are as far as possible away from the mounting holes and the connection between the connection seat 3 and the orthosis body, in order to ensure the installation strength of the key components of the orthosis. As mentioned above, after the pressing rod 6 moves to cause the press disc 63 to press the annular airbag 7, the pressing rod 6 needs to be fixed by a fixing structure to avoid the annular airbag 7 from springing back. In this embodiment, as shown in FIG. 10, as a specific fixing structure, a threaded section 65 is provided on the side of the pressing rod 6 and a threaded hole 53 is provided in the center of the connection seat 3, the threaded section 65 screwed into the threaded hole 53 to form the fixing structure. In this structure, the threaded section 65 and the threaded hole 53 cooperate to drive the pressing rod 6 to slide when the pressing rod 6 is rotated, and the pressing rod 6 is fixed when it stops rotating. This structure can enable the position of the pressing rod 6 to be steplessly adjusted, with higher accuracy of adjustment and for better correction effect.

In order to prevent the threaded hole 53 from being disengaged from the threaded section 65 due to excessive rotation of the pressing rod 6, a limit block 8 is provided in the orthosis, and the end of the pressing rod 6 away from the press disc 63 extends out of the threaded hole 53, to which end the limit block 8 is fixedly connected. The limit block 8 and the pressing rod 6 are preferably connected together by means of glue or screws, and the pressing rod 6 can be driven to rotate by rotating the limit block 8 to realize the movement and stop of the pressing rod 6. In the above preferred solution, in order to ensure the followability of the limit block 8 and the pressing rod 6, a positioning structure may be provided between them to ensure the synchronous rotation of the two. For example, the positioning structure may include a polygonal through hole provided in the center of the limit block 8 and a polygonal post provided in the center of the pressing rod 6, so that the synchronous rotation can be realized by inserting the polygonal post into the polygonal through hole. Alternatively, foresaid technical purpose can also be achieved at the eccentric position by means of a positioning pin or the like. The limit block 8 may be a structure protruding from the connecting seat 3. According to this structure, the limit block 8 can be rotated by applying a force on the side of the limit block 8. The limit block 8 may also be arranged inside the connection base 3, or may be a structure in which the outer side of the limit block 8 is flush with the surface of the connection base 3. In this structure, a slot needs to be provided in the outer side of the limit block 8 so that the user can use the corresponding tools to drive the limit block 8 to rotate. The slot may be in the form of a straight line, a cross pattern or an inner hexagon, which is convenient for using external tools. Scales can also be provided on the surface of the connecting seat 3 or orthosis body 1 to indicate the rotation angle of the limit block 8 to the user, facilitating adjustment by users with insufficient professional knowledge.

Embodiment 3

Figure 11:
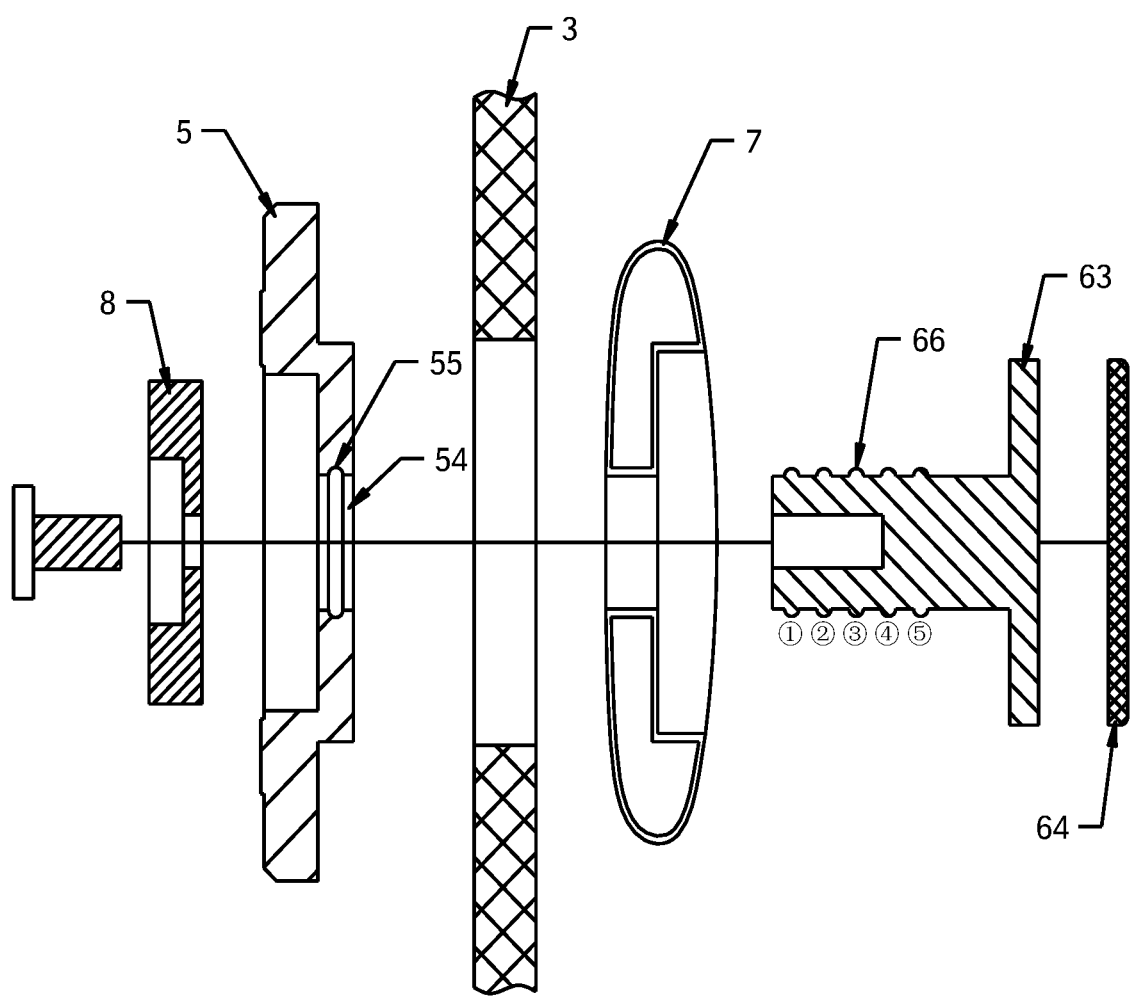
FIG. 11 is an exploded cross-sectional view of the components of the adjustment device in Embodiment 3.

An adjustable scoliosis orthosis is shown in FIG. 11. Unlike Embodiment 2, according to the specific fixing structure of Embodiment 3, the connecting seat 3 is provided with a through hole 54, wherein the side wall of the through hole 54 is provided with a snap slot 55, and wherein a plurality of snap rings 66 are provided on the side of the pressing rod 6, one of the plurality of snap rings 66 snapped with the slot 55 to form the fixing structure. By pushing the pressing rod 6, the snap ring 66 is pushed out of the slot 55 and the next snap ring 66 is pressed into the slot 55, so that the position of the pressing rod 6 can be adjusted stepwise. In this structure, the snap ring 66 can be graded according to the user's situation. The user only needs to move the pressing rod 6 according to the wearing time to snap the corresponding snap ring 66 into the slot 55. For example, as shown in FIG. 11, several snap rings 66 are numbered. When wearing the orthosis for the first time, the user adjusts the pressing rod 6 to snap the snap ring 66 numbered ① into the slot 55. After one month of wearing, the user adjusts the pressing rod 6 to snap the snap ring 66 numbered ② into the slot 55. After two months of wearing, the user adjusts the pressing rod 6 to snap the snap ring 66 numbered ③ into the slot 55, and so on. In this way, the problem that users with insufficient professional knowledge are not able to adjust the position of pressing rod 6 by themselves, resulting in unsatisfactory correction effect is avoided. The optimal correction effect can be achieved as long as the users follow the use instructions.

Embodiment 4

As a preferred implementation of the Embodiment 1 and different from Embodiment 2, the internal gas pressure of the airbag structure 7 is adjusted by changing the internal gas volume.

In this embodiment, an air pressure detection device can be used to detect the gas pressure inside the airbag structure 7. The pressure can be increased quickly by means of an external gas source, and reduced conveniently through deflation, so that the effect on different human bodies is more targeted.

Figure 13:
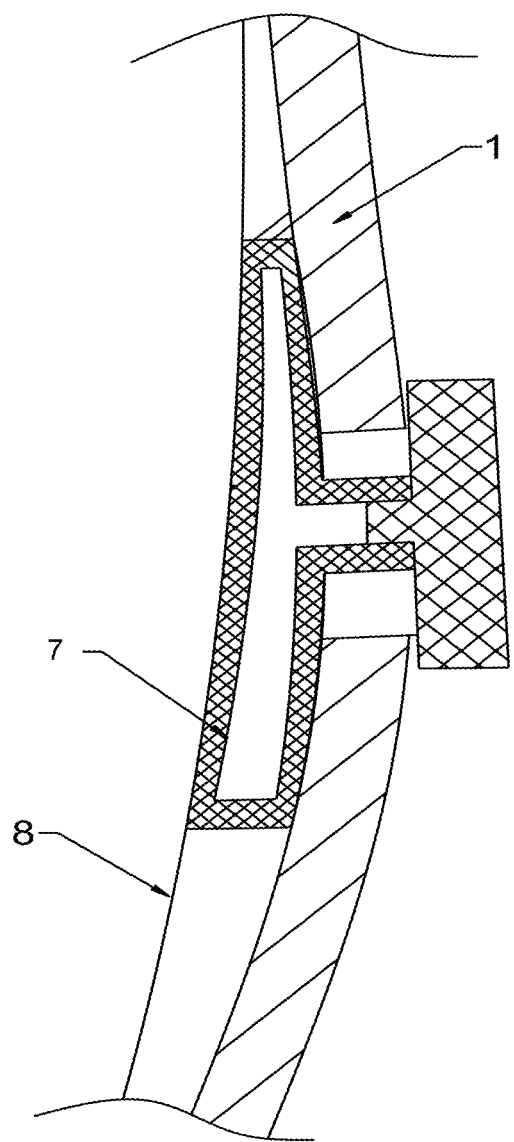
FIG. 13 is a schematic diagram of the use of a special-shaped airbag structure in Embodiment 4.

Further, as shown in FIG. 13, the airbag structure 7 comprises an inflation end for gas volume adjustment by supplying gas in and out of the interior of the airbag. For the above structure, the gas volume may be determined in advance, or it can also be adjusted after the user puts on the orthosis, both falling into the protection scope of the present invention.

In addition, in the present invention, a special-shaped airbag structure 7 can also be provided. FIG. 13 shows a special-shaped airbag structure 7 that can adapt to the human body boundary 8, in which the inflation end may be blocked by a plug or a one-way valve.

The present invention also relates to a method for using an adjustable scoliosis orthosis, which is applicable to the adjustable scoliosis orthosis described in the above embodiments, including the following steps:

causing a user to put on an orthosis body 1 without mounting holes, marking the position of the mounting holes according to correction needs of the user's torso, and then removing the orthosis body to machine the mounting holes; and fixing an adjustment device at the position where the mounting holes are provided.

Here we take Embodiment 2 above as an example. The connecting seat 3 is placed to the installation holes from the outside of the orthosis body 1, and the connecting seat 3 and the orthosis body 1 are connected together; then the annular airbag 7 is sleeved onto the pressing rod 6, and then the pressing rod 6 is passed through the mounting hole from the inside of the orthosis body 1 and mounted to the connecting seat 3.

Afterwards, the user puts on the orthosis body 1, adjusts the position of the pressing rod 6 so that the annular airbag 7 exerts a force on the user's body to realize the correction function.

In the present invention, the shape data of the user's torso can be obtained through 3D scanning technology and the orthosis body 1 may be produced by 3D printing using engineering plastics based on the scanned shape data. The specific methods and steps of scanning and 3D printing are prior art, so they will not be described in detail. In the present invention, the mounting holes are formed at a later phase, effectively reducing the processing difficulty and cost of the orthosis body 1. The processing difficulty of the mounting holes is extremely low, and the processing position of the mounting holes can be determined more accurately after the orthosis body 1 is worn.

The basic principles, main features and advantages of the present invention have been shown and described above. Those skilled in the industry should understand that the present invention is not limited by the foregoing embodiments. The foregoing embodiments and descriptions only illustrate the principles of the present invention. Without departing from the spirit and scope of the present invention, the present invention will have various changes and improvements, which fall within the scope of the claimed invention. The scope of protection claimed by the present invention is defined by the appended claims and their equivalents.

The invention claimed is:

1. An adjustable scoliosis orthosis comprising:
an orthosis body configured to be worn around a user's torso, the orthosis body having an inner surface shaped to conform to the user's torso and an opening configured to allow the torso to enter and exit;
a connecting mechanism arranged across the opening for selectively securing and adjusting a fit of the orthosis around the torso; and
an adjustable pressure system comprising:
an annular airbag assembly positioned within the orthosis body and configured to apply localized corrective pressure to targeted regions of the user's torso; and
a pressure adjustment mechanism comprising a pressing rod extending through a connecting seat fixed to the orthosis body, the pressing rod having a press disc at one end, wherein the annular airbag assembly is sleeved on the pressing rod and positioned between the press disc and the orthosis body,
wherein the pressing rod is adjustable to vary a position of the press disc relative to the annular airbag assembly, thereby altering an internal volume and pressure of the annular airbag assembly to provide adjustable, localized corrective force on the user's torso, wherein the annular airbag assembly further comprises an inflation end configured to allow adjustment of the internal volume within the annular airbag assembly; and wherein the inflation end of the annular airbag assembly is provided with a valve mechanism to allow a controlled inflow and outflow of gas to the annular airbag assembly.

2. The adjustable scoliosis orthosis of claim 1, wherein the annular airbag assembly is provided with a countersunk structure in a middle of the annular airbag assembly, into which the press disc fully extends.

3. The adjustable scoliosis orthosis of claim 2, wherein the press disc is provided with a flexible structure on a surface facing the orthosis body.

4. The adjustable scoliosis orthosis of claim 1, wherein an outermost diameter of the annular airbag assembly is larger than a diameter of a mounting hole provided on the orthosis body.

5. The adjustable scoliosis orthosis of claim 4, wherein the outermost diameter of the annular airbag assembly is designated as A, and a diameter of the press disc is designated as B, wherein $A > B > A/2$.

6. The adjustable scoliosis orthosis of claim 1, wherein the pressing rod is provided with a threaded section, and the connecting seat is provided with a threaded hole, wherein the threaded section is screwed into the threaded hole to form a fixing structure that secures the pressing rod in position.

7. The adjustable scoliosis orthosis of claim 6, further comprising a limit block connected to an end of the pressing rod distal from the press disc, the limit block preventing over-rotation of the pressing rod relative to the threaded section.

8. The adjustable scoliosis orthosis of claim 6, wherein the pressing rod is steplessly adjustable within the threaded hole of the connecting seat to provide incremental adjustments to the position of the press disc relative to the annular airbag assembly.

9. The adjustable scoliosis orthosis of claim 1, wherein the connecting mechanism comprises two external structures on both sides of the opening of the orthosis body, and an adjustment structure is connected to the external structures to adjust a size of the opening of the orthosis body.

10. The adjustable scoliosis orthosis of claim 9, wherein the adjustment structure comprises two flexible structures, a tightening belt, and a winding wheel, wherein the tightening belt is arranged to run through perforations in the flexible structures, and the winding wheel is fixedly connected to the orthosis body to adjust a tension of the tightening belt by adjusting a winding length of the belt.

11. The adjustable scoliosis orthosis of claim 1, wherein the pressing rod is configured to be rotated to adjust the position of the press disc, and the orthosis further comprises a locking mechanism to secure the pressing rod in a desired position.

12. The adjustable scoliosis orthosis of claim 1, wherein the orthosis body is provided with a plurality of hollow holes to increase breathability during use.

* * * * *